United States Patent [19]

Suzuki et al.

[11] Patent Number: 4,870,011
[45] Date of Patent: Sep. 26, 1989

[54] METHOD FOR OBTAINING LIPIDS FROM FUNGUS BODIES

[75] Inventors: Osamu Suzuki, Tsuchiura; Toshihiro Yokochi, Sakura, both of Japan

[73] Assignee: Director General of Agency of Industrial Science and Technology, Tokyo, Japan

[21] Appl. No.: 905,589
[22] PCT Filed: Dec. 13, 1985
[86] PCT No.: PCT/JP85/00685
  § 371 Date: Aug. 22, 1986
  § 102(e) Date: Aug. 22, 1986
[87] PCT Pub. No.: WO86/04353
  PCT Pub. Date: Jul. 31, 1986

[30] Foreign Application Priority Data
  Jan. 22, 1985 [JP] Japan .................. 60-10283
  Feb. 21, 1985 [JP] Japan .................. 60-33130

[51] Int. Cl.$^4$ ............................... C12P 7/64
[52] U.S. Cl. .................. 435/134; 260/412.8; 260/420
[58] Field of Search ............ 435/134; 260/412, 412.8, 260/420

[56] References Cited
U.S. PATENT DOCUMENTS
  4,235,796  11/1980  Paulicka .................. 260/412.8

FOREIGN PATENT DOCUMENTS
  0125764  11/1984  European Pat. Off. .
  0155420   9/1985  European Pat. Off. .
   889959   1/1944  France .
  56-115399  9/1981  Japan .
  57-144986  9/1982  Japan .
  59-130191  7/1984  Japan .
  59-205979 11/1984  Japan .
   336273  10/1930  United Kingdom ............ 260/412.8

OTHER PUBLICATIONS

Farag et al., "The Lipids of Various Fungi Grown on an Artificial Medium", JAOCS, Jul. 1981, pp. 765-781.
Kato et al., "High-Linolenic Oils from Five Species of Japanese Plants", JAOCS, Sep. 1981, pp. 866-867.

Primary Examiner—Barry S. Richman
Assistant Examiner—Timothy M. McMahon
Attorney, Agent, or Firm—Hopgood, Calimafde, Kalil, Blaustein & Judlowe

[57] ABSTRACT

The invention relates to a procedure of obtaining a lipid mixture rich in the content of γ-linolenic acid or glycerides thereof from cultured fungus bodies of a filamentous Mortierella fungus. The invention proposes, on one hand, to fractionally extract the lipid mixture from the fungus bodies under mechanical disintegration in two steps first with an alcohol containing water to give a fraction rich in the polar lipids and then with a hydrocarbon solvent, e.g. hexane, to give a fraction lean in the polar lipids. The invention proposes, on the other hand, to enrich a lipid mixture relative to γ-linolenic acid by fractionally crystallizing a part of a starting lipid mixture in a solution of a specified solvent so that the uncrystallized fraction in the mother liquor contains a lipid mixture in which the content of γ-linolenic acid is remarkably increased in comparison with the starting lipid mixture.

7 Claims, No Drawings

METHOD FOR OBTAINING LIPIDS FROM FUNGUS BODIES

TECHNICAL FIELD

This invention relates to a method for obtaining lipids from cultured fungus bodies or, more particularly, to a method for obtaining certain particularly useful lipids, e.g. γ-linolenic acid glycerides, from cultured bodies of filamentous fungi belonging to the genus of *Mortierella*.

BACKGROUND ART

As is known, γ-linolenic acid is one of the essential fatty acids which must be contained in daily foods of human life in the form of the acid per se or a lipid containing the same. It is therefore highly desirable to establish a way for obtaining γ-linolenic acid to be used for the enrichment of foods. Conventionally, γ-linolenic acid or a lipid containing the same is obtained from seeds of evening primrose (*Oenotbera biennis* L.) but this method is of very low productivity as an industrial method. Accordingly, attempts have been made eagerly to discover an alternative plant which produces seeds containing an oil much richer in the content of γ-linolenic acid or a lipid containing the same than the seeds of evening primrose [see, for example, Journal of American Oil Chemists Society, volume 60, page 1858 (1983)]. Despite the great efforts with this purpose, no very promising plant has yet been discovered and all of the hitherto proposed plants are very specific with low availability. Therefore, industrial applicability can hardly be found in this direction of obtaining γ-linolenic acid with sufficient productivity from plant seeds not only in respect of growing such a special plant but also in respect of collecting the seeds therefrom in large quantities.

On the contrary, there may be a potential possibility for the industrial production of γ-linolenic acid if a microbiological process can be developed and established by culturing a microorganism containing lipids rich in the content of γ-linolenic acid in the microbial bodies. This is because the culture of microorganisms requires no solar energy and can be performed as a factory process so that the process is free from the restrictions imposed by the availability of a large area of plant site and the meteorological conditions to give a high and stable productivity and enjoys free controllability of the production rate.

It has been discovered that certain filamentous fungi belonging to the genus of *Mortierella* are very promising in this regard including the species of *M. isabellina, M. vinacea, M. ramanniana, M. ramanniana* var. *angulispora, M. nana* and the like. Namely, it has been discovered that the fungus bodies of these filamentous fungi cultured in a culture medium containing carbohydrates as the carbon source contain 30 to 60% of lipids on the dry basis of which the content of γ-linolenic acid is as high as 2 to 12% or, in most cases, 7 to 8% in the overall fatty acid content. Further advantageously, these filamentous fungi can be cultured in an unusually high density in a culture medium so that the productivity of γ-linolenic acid by the microbiological process can be increased very greatly. Conventionally, the lipids contained in the fungus bodies are extracted as a whole by homogenizing the fungus bodies in a solvent mixture of chloroform and methyl alcohol so that the content of the γ-linolenic acid glycerides in the extracted lipids is also limited.

Although the above mentioned microbiological process is very promising as an industrial method for the production of γ-linolenic acid, the content of γ-linolenic acid in the fungus body lipids is still not high enough to ensure the usefulness of the fungus-origin lipids extracted in a conventional manner as such as a material for food enrichment or other medicinal purposes. When the culturing conditions of the filamentous fungus are modified with an object to increase the growth rate of the fungus bodies or to obtain the fungus bodies containing an increased overall amount of lipids, in particular, it is sometimes difficult to have the content of γ-linolenic acid in excess of 3 to 6% in the overall fatty acids. Nevertheless, no efficient method has yet been developed for the selective extraction of the lipids from the fungus bodies into fractions rich and lean in the content of γ-linolenic acid or no convenient method for upgrading the lipids extracted from the fungus bodies is known in respect of the content of γ-linolenic acid.

Accordingly, it would be very desirable to develop a method for obtaining lipids containing an increased amount of γ-linolenic acid from the bodies of cultured filamentous fungi. Such a method would be useful also for the enrichment of the lipids obtained from the seeds of plants, e.g. evening primrose, in respect of the content of γ-linolenic acid or glycerides of the same.

DISCLOSURE OF THE INVENTION

The scope of the present invention pertains, in one aspect, to the process for the solvent extraction of the lipids from the fungus bodies of cultured filamentous fungi in which the lipids can be extracted into fractions rich and lean in the content of the polar lipids or the neutral lipids.

As the other aspect of the scope of the inventive method, the invention proposes a very efficient method for the enrichment of lipids, i.e. glycerides, extracted from the cultured fungus bodies in respect of the content of γ-linolenic acid or glycerides of the same.

Thus, the method of the present invention comprises:

(a) disintegrating fungus bodies of a filamentous fungus belonging to the genus of *Mortierella* containing lipids in a liquid medium of an alcohol containing water or in the presence of water to cause fractional extraction of a part of the lipids contained in the fungus bodies into the liquid medium;

(b) separating the liquid medium containing the extracted lipids from the fungus bodies to give a first fractional extract;

(c) contacting the fungus bodies separated from the first fractional extract with a hydrocarbon solvent to cause extraction of the residual fraction of the lipids contained in the fungus bodies; and (d) separating the hydrocarbon solvent containing the extracted lipids from the fungus bodies depleted of the lipids to give a second fractional extract.

In the above described two-step extraction process of the invention, it has been established that the first fractional extract is rich in the content of the polar lipids including glycerides of γ-linolenic acid in comparison with the second fractional extract.

The invention also provides a method for the enrichment of the glycerides of γ-linolenic acid in a lipid mixture which may be the first or the second fractional extract obtained in the above described two-step extraction process or even in the lipid mixture obtained as a whole extract from the cultured fungus bodies. The method comprises:

(e) dissolving a mixture of lipids containing glycerides of γ-linolenic acid in an organic solvent selected from the group consisting of hexane, acetone, ethyl alcohol and petroleum ether to give a solution;

(f) chilling the solution to precipitate a part of the lipids in a crystalline form; and (g) separating the precipitated lipids from the mother liquor which is a solution of lipids containing the glycerides of γ-linolenic acid in an increased content.

BEST MODE FOR CARRYING OUT THE INVENTION

As is understood from the above description, the fungus bodies obtained by culturing a fungus belonging to the genus of Mortierella serve as the starting material used in the two-step extraction process of the invention. The fungus bodies can readily be separated from the culture medium by filtration or centrifugal separation.

In the first step of the two-step extraction, the fungus bodies are subjected to the solvent extraction, in the above mentioned step (a), with an alcohol as the extraction solvent which should contain or should be used in the presence of water. While the starting material in this case may be a cake of the fungus bodies obtained by separating from the culture medium by filtration or centrifugal separation either as wet containing 50 to 80% of water or after drying, it would be a convenient and economical way that the wet cake is used as such so as to save the costs for the drying process. It is essential in this step that the fungus bodies are disintegrated under a mechanical action to cause crushing or grinding of the bodies in the alcoholc extraction medium in order to increase the efficiency of the extraction. Various types of known extraction apparatuses can be used for the purpose to exhibit the desired crushing action on the fungus bodies including the wet-process pulverizing machines such as ball mills, frictional disk mills, Henschel mixers and the like. When a wet cake of the fungus bodies is added to the alcoholic medium in the pulverizing apparatus and the machine is operated, the fungus bodies are at least partly destroyed or broken by the compressive or frictional mechanical force. It is noteworthy in this case that the crushing or grinding action on the fungus bodies should not be conducted excessively prolongedly or intensively to cause too fine disintegration of the fungus body in order to avoid possible difficulties encountered in. The subsequent step (b) for the separation of the liquid medium and the fungus bodies. In this regard, the operation of the pulverizing machine should be terminated when all of the fungus bodies have been partly broken on the cell walls but substantially no change is found in the dimensions of the fungus bodies as inspected microscopically.

The alcoholic solvent used as the extraction medium should be a lower alcohol miscible with water exemplified by methyl, ethyl and propyl alcohols although ethyl alcohol is preferred in view of the safety to the human body. The amount of the alcoholic solvent added to the fungus bodies should be in the range from 2 to 7 parts by weight or, preferably, from 3 to 6 parts by weight per part of the fungus bodies on the dry basis.

It is essential in this first-step extraction that the alcoholic solvent as the extraction medium should contain water or the extraction should be performed in the presence of water so that the alcoholic solvent can be hydrous containing the water taken therein. The amount of water to be contained in the alcoholic solvent or to be present in the extraction system should be in the range from 0.2 to 0.7 part by weight or, preferably, from 0.3 to 0.6 part by weight per part by weight of the alcoholic solvent on the anhydrous basis. Such an amount of water can be supplied separately in a calculated weight when the fungus bodies are completely dry but the amount of separate addition of water should be reduced when the fungus bodies contain more or less of water as is the case when a wet cake of the fungus bodies is used as such.

The above described first-step extraction is usually effective to extract 90% or more of the polar lipids contained in the fungus bodies into the liquid extraction medium. The neutral lipids in the fungus bodies are also extracted partly in this first-step extraction so that the overall extraction of the lipids in this first extraction usually reaches from 5 to 30% by weight or, in most cases, from 8 to 25% by weight of the overall lipid content in the fungus bodies.

In the step (b) to follow, the extraction mixture obtained in the above described step (a) is subjected to the solid-liquid separation into the fungus bodies in a caked form and the liquid extraction medium containing the extracted lipids in the hydrous alcoholic solvent as the first fractional extract. The method of this solid-liquid separation may be conventional including filtration and centrifugal separation.

The cake of the fungus bodies obtained in the step (b) mentioned above is then subjected to a second extraction treatment as the step (c) in which the extraction solvent is a hydrocarbon solvent. Preferably, this second extraction is performed also under a concurrent crushing or grinding mechanical action to further disintegrate the fungus bodies in the same manner as in the first step extraction although the crushing or grinding action can be omitted when the fungus bodies have already been disintegrated to a sufficient degree in the step of the first extraction.

Suitable hydrocarbon solvents used in this second-step extraction include n-hexane, cyclohexane and the like. The amount of the hydrocarbon solvent added to the fungus bodies should be in the range from 2 to 8 parts by weight or, preferably, from 3 to 6 parts by weight per part by weight of the starting fungus bodies on the dry basis. It is noted that the extraction medium in this second-step extraction should be as highly as possible anhydrous in order to increase the efficiency of the lipid extraction. In this regard, the amount of water contained in the extraction system should not exceed 0.05 part by weight or, preferably, 0.03 part by weight per part by weight of the hydrocarbon solvent. The extent of control of the water content depends on the degree of removal of the liquid extraction medium from the cake of the fungus bodies in the preceding step (b). In this regard, it is an advantageous way that the wet cake obtained in the step (b) is washed in advance with an anhydrous alcoholic solvent prior to the secondstep extraction. In this manner, the lipids contained in the fungus bodies after the first-step extraction are almost completely extracted into the hydrocarbon solvent.

The thus obtained extraction mixture is then subjected to the second solid-liquid separation in the following step (d) into a cake of the fungus bodies to be discarded and the liquid medium containing the extracted lipids as the second fractional extract. The lipids in this second fractional extract are mainly composed of the neutral lipids. The method of the solid-liquid separation in this step may also be conventional as in the step (b).

Each of the first and the second fractional extracts is further subjected to the recovery of the lipids contained therein. The process therefor may be conventional. For example, the second fractional extract containing almost exclusively the neutral lipids is purified using an adsorbent such as active charcoal and activated clay to have the polar lipids adsorbed thereon and the neutral lipids can be obtained by evaporating the hydrocarbon solvent from the solution in a considerably pure form containing almost no polar lipids.

As is described above, the fungus bodies after the first fractional extraction are almost completely freed from the polar lipids so that the lipid mixture obtained by the second fractional extraction is composed almost exclusively of the neutral lipids alone. Therefore, the extract obtained in the second extraction can be processed into an oleaginous product by a simple adsorption treatment for removing the trace amount of the polar lipids followed by the evaporation of the hydrocarbon solvent. On the other hand, the fractional extract obtained in the first extraction contains both neutral and polar lipids and can be separated further into the respective classes of the lipids. It should be noted that the amount of the mixture of the neutral and polar lipids recovered in the first extraction is usually as small as 20% or less of the overall content of lipids in the fungus bodies. This reduction in the amount of the mixture composed of neutral and polar lipids provides a great advantage when the mixture is desired to be further separated into the neutral and the polar lipids in respect of the possibility of using small apparatuses for the process of separation which may be any of conventional ones including the method of solvent extraction using hexane, acetonitrile and the like as the extraction solvent and a method of adsorption using silica, alumina and the like as the adsorbent.

In the above described two-step extraction, moreover, the alcoholic solvent and the hydrocarbon solvent are used not as a mixture but used separately so that the intrinsic performance of the respective solvents for the extraction of the particular type of the lipids can be fully exhibited. As a result, an advantage is obtained that the fungus bodies may not be disintegrated very finely but the efficiency of extraction is high enough even with a very limited mechanical action for the disintegration of the fungus bodies merely by compression under pressure or partial break of the bodies under friction resulting in a great saving of the costs for the disintegration of the fungus bodies. The separate use of the two different solvents is also advantageous in respect of the easiness of recovering the extracted lipids from the extract solution in comparison with the conventional method of using a solvent mixture..

In connection with the recovery of the valuable $\gamma$-linolenic acid and glycerides thereof from a mixture with other types of lipids, the present invention provides a very efficient method therefor in comparison with prior art methods. The method has been established on the base of an unexpected discovery that, when a mixture of lipids is dissolved in a specific organic solvent in a suitable concentration and the solution is chilled at or below a certain temperature, crystalline precipitates mainly composed of triglycerides are formed in the solution to effect fractionation into a crystallized and uncrystallized fractions while the latter fraction is enriched in the content of the glycerides of $\gamma$-linolenic acid.

The lipid mixture to be subjected to the fractional crystallization may be a whole extract obtained from the fungus bodies in a conventional method of extraction or may be the first or the second extract obtained in the above described two-step extraction. The solvent used for dissolving the lipid mixture is selected from the group consisting of hexane, acetone, ethyl alcohol and petroleum ether or a mixture thereof. The concentration of the lipids in the solution should be in the range from 5 to 50% or, preferably, from 5 to 40% on a weight/volume basis, i.e. in grams of the solute in 100 ml of the solvent. When such a solution is chilled at a temperature in the range from $+5°$ to $-30°$ C. or, preferably, from $5°$ to $-20°$ C., partial crystallization of the lipids can readily take place in the solution. The precepitates of the crystallized lipids can be readily separated from the solution or mother liquor by any conventional method of solid-liquid separation such as filtration under reduced pressure or under pressurization and centrifugal separation. The solution or mother liquor obtained by removing the crystallized lipids is then subjected to distillation to evaporate the solvent leaving a lipid mixture containing the glycerides of $\gamma$-linolenic acid in a remarkably increased concentration.

The above described method of fractional crystallization is so effective despite the simple and easy procedure thereof that a lipid mixture including the glycerides of $\gamma$-linolenic acid obtained by this method contains $\gamma$-linolenic acid in a concentration of 6.5% by weight or higher even when the starting lipid mixture is lean in the content of $\gamma$-linolenic acid as in the lipid mixture extracted from the fungus bodies of the Mortierella fungi of which the content of $\gamma$-linolenic acid is usually in the range of 3 to 6% by weight.

The lipid mixture obtained by this method and enriched in the content of $\gamma$-linolenic acid is very useful as a medicine or as an additive of foods since $\gamma$-linolenic acid, like linoleic acid, is one of the essential fatty acids which cannot be synthesized in the body of mammalian animals and must be externally supplied in the form of the acid or glyceride. $\gamma$-Linolenic acid plays a very important physiological role in a living body as a precursor of arachidonic acid through an intermediate of bishomo-$\gamma$-linolenic acid while bishomo-$\gamma$-linolenic acid and arachidonic acid are the precursors of prostaglandins $E_1$ and $F_{1\alpha}$ and $E_2$ and $F_{2\alpha}$, respectively.

In the following, examples are given to illustrate the method of the invention in more detail. In the examples, the percentage expression is always on a weight basis if not otherwise mentioned.

EXAMPLE 1

A fungus of the genus of Mortierella indicated in Table 1 by the IFO strain No. was cultured in a 30-liter culture tank and the fungus bodies were separated from the culture medium and dehydrated by centrifugal separation into a fungus body cake containing 50 to 70% of water. After sterilization of the wet fungus body cake in an autoclave at 120° C. for 10 minutes under a pressure of 2 atmospheres, the wet cake was subjected to the extraction of the lipids in the following manner.

Thus, 1.0 to 1.7 kg of the wet cake was taken in a stainless steel-made ball mill of 6 liter capacity together with 2 liters of ethyl alcohol as the extraction solvent and the ball mill was driven for 4 hours to simultaneously effect disintegration of the fungus body and extraction of the lipids into the solvent. The extract solution was filtered to be freed of the disintegrated fungus bodies and the fungus bodies containing 3.4% of water were further subjected to the second-step extraction for 7 hours with 2 liters of hexane as the solvent in the same manner as in the first-step extraction with ethyl alcohol. The data obtained as a result of the two-step extraction process are summarized in Table 1 below. The overall content of lipids in the starting fungus bodies tabulated in the table was obtained by the homogenizing extraction using a 2:1 by volume mixture of chloroform and methyl alcohol and the water content by weight in the first-step extraction was calculated and given in % by weight based on the amount of the ethyl alcohol.

Table 2 is for the % contents of the polar and neutral lipids and the % composition of the neutral lipids divided into different lipid types.

TABLE 2

|  |  | First fractional extract | Second fractional extract |
|---|---|---|---|
| Polar lipids, % | | 14.1 | 0.8 |
| Neutral lipids, % | | 85.9 | 99.2 |
| In the neutral lipid fraction, % | Triglycerides | 4.4 | 89.3 |
| | Diglycerides | 66.6 | 89.3 |
| | Monoglycerides | (trace) | (trace) |
| | Free fatty acids | 23.6 | 0.3 |
| | Free sterols | 4.7 | 9.4 |
| | Sterol esters | 0.7 | (trace) |

TABLE 1

| Experiment No. | | 1 | 2 | 3 | 4 | 5 | 6 | 7 |
|---|---|---|---|---|---|---|---|---|
| IFO strain No. of fungus | | 6738 | 8187 | 8187 | 8187 | 8187 | 7824 | 7824 |
| Fungus body cake | Weight as wet, g | 1350 | 1292 | 1221 | 1280 | 1348 | 1626 | 1055 |
| | Water content, % | 57.3 | 70.9 | 70.9 | 58.6 | 58.6 | 66.7 | 66.1 |
| | Weight as dry, g | 576 | 376 | 355 | 530 | 558 | 542 | 358 |
| | Overall lipid content, % | 51.1 | 46.8 | 46.8 | 45.6 | 45.6 | 39.5 | 40.4 |
| First-step extraction | Water content, % | 49.0 | 54.6 | 54.9 | 47.5 | 50.1 | 68.7 | 44.2 |
| | Extracted lipids net weight, g | 26.5 | 23.7 | 22.0 | 51.5 | 24.9 | 36.5 | 30.3 |
| | % of dry cake | 4.6 | 6.3 | 6.2 | 9.7 | 4.5 | 6.7 | 8.5 |
| | lipid recovery, % | 9.1 | 13.5 | 13.2 | 21.3 | 9.8 | 17.0 | 21.0 |
| Extracted lipids in second-step extraction | net weight, g | 245.0 | 152.5 | 137.2 | 187.8 | 172.6 | 162.8 | 103.9 |
| | % of dry cake | 42.5 | 40.6 | 38.6 | 35.4 | 37.8 | 30.0 | 29.0 |
| | lipid recovery, % | 83.2 | 86.3 | 82.5 | 77.6 | 83.0 | 75.9 | 71.8 |
| Overall lipid recovery, % | | 92.3 | 99.8 | 95.7 | 98.9 | 92.8 | 92.9 | 92.8 |

As is shown by the results in Table 1, the amount of the extracted lipids in the first-step extraction with ethyl alcohol was in the range from 4.5 to 9.7% of the dry fungus body cake and was subject to some variation depending on the fungus strain, lipid and water content in the fungus body cake and other parameters while the lipid recovery was in the range from 9.1 to 21.3% or mostly 20% or less of the overall lipid content in the fungus body cake. In the second-step extraction with hexane, on the other hand, the amount of the extracted lipids was high in the range from 29.0 to 42.5% based on the dry fungus body cake so that the overall lipid recovery could be as high as 92% or more with little loss of the lipids contained in the fungus bodies.

In the next place, the first and the second fractional extracts of the lipids obtained in Experiment No. 2 shown in Table 1 were subjected to the analyses for the % compositions of different types of the lipids and different kinds of the fatty acids so as to confirm the effect of fractionation in the first-step and second-step extractions. Firstly, each of the lipid extracts was subjected to the column chromatography according to the procedure described in Yukagaku, volume 30, page 854 (1981) using a silica gel as the stationary phase carrier and divided into the fractions of neutral and polar lipids to give the % ratio of each fraction. The fraction of the neutral lipids obtained in each column-chromatographic separation was then subjected to the analysis of the lipid type by the method of thin-layer chromatography combined with densitometry in a procedure described in Yukagaku, volume 28, page 59 (1979). Further, each of the fractions was subjected to the gas-chromatographic analysis for the contents of different fatty acids in a procedure described in Yukagaku, volume 30, page 854 (1981). The results of these analyses are summarized in Table 2 and Table 3 below, of which

TABLE 3

| | First fractional extract | | Second fractional extract | |
|---|---|---|---|---|
| Fatty acid | Polar lipids | Neutral lipids | Polar lipids | Neutral lipids |
| Myristic acid, % | 1.0 | 1.3 | 3.7 | 1.1 |
| Palmitic acid, % | 21.5 | 28.2 | 18.9 | 30.9 |
| Palmitooleic acid, % | 2.3 | 1.5 | 1.5 | 0.5 |
| Stearic acid, % | 2.1 | 4.2 | 3.5 | 5.6 |
| Oleic acid, % | 33.7 | 43.0 | 38.9 | 45.7 |
| Linoleic acid, % | 22.4 | 12.6 | 17.7 | 9.7 |
| γ-Linolenic acid, % | 15.1 | 9.2 | 11.7 | 6.2 |

As shown by the results in Table 2, the first fractional extract, i.e. The extract obtained with ethyl alcohol, contained a much larger amount, i.e. 14 1%, of the polar lipids than the second fractional extract, i.e. the extract obtained with hexane, in which the content of the polar lipids was only 0.8%, indicating the great enrichment of the first fractional extract in the content of the polar lipids. The neutral lipids in the first fractional extract was mainly composed of the diglycerides and free fatty acids, i.e. 66.6% of the former and 23.6% of the latter, accompanied by an extremely small amount, i.e. 4.4%, of the triglycerides. Free sterols were also concentrated in this fraction of neutral lipids. These results indicate the selective extraction of the lipids having a polar or functional group with strong affinity with water in the first-step extraction with a hydrated ethyl alcohol as the solvent. In connection with the contents of different fatty acids, as is shown in Table 3, the contents of γ-linolenic acid and linoleic acid were much higher in both of the polar and neutral lipid fractions from the first-step extraction than in the fractions from the second-step extraction. On the contrary, the contents of palmitic, stearic and oleic acids are lower in the first fractional extract with ethyl alcohol than in the second fractional extract with hexane.

Turning now to the composition of the second fractional extract with hexane, the content of the polar lipids therein is extremely small as is shown in Table 2 and the fraction is composed almost exclusively of the neutral lipids. Further, the neutral lipid fraction is mainly composed of the triglycerides with only a minor amount, i.e. 9%, of the diglycerides and trace amounts of free fatty acids and free sterols so that the fraction can be used as such as an oleaginous product. Further, the content of γ-linolenic acid in the neutral lipid fraction in this second fractional extract is as high as 6.2% to be comparable with the evening primrose oil so that the second fractional extract can be a promising source material for obtaining γ-linolenic acid or lipids thereof in a purified or enriched form.

The results of Table 3 also indicate that the first fractional extract with ethyl alcohol can be used as a source material for obtaining polar lipids, e.g. phospholipids, glycolipids and the like, of high γ-linolenic acid content. Further, the neutral lipid fraction of the first fractional extract with ethyl alcohol can be used as a source material for the enrichment of γ-linolenic acid or a diglyceride mixture of high γ-linolenic acid content.

EXAMPLE 2

A fungus of *Mortierella ramanniana* var. *angulispora* IFO 8187 was cultured in a 30-liter culture tank at 30° C. for 72 hours and the thus obtained fungus body cake containing γ-linolenic acid in a relatively low content was used as the source material for the enrichment of γ-linolenic acid-containing lipids by the method of fractional crystallization.

The gas chromatographic analysis of the fungus body lipid mixture for the fatty acid composition indicated that the mixture was composed of various fatty acids including: 30.5% of palmitic acid; 1.9% of palmitooleic acid; 4.6% of stearic acid; 45.7% of oleic acid; 9.7% of linoleic acid; and 6.0% of γ-linolenic acid. Further, the thin layer chromatographic analysis for the types of glycerides therein indicated that the mixture was composed of 81.8% of triglycerides, 3.4% of 1,3-diglycerides and 13.7% of 1,2-diglycerides. High-performance liquid chromatographic analysis was undertaken for the respective species of the triglycerides and diglycerides relative to the combination of the fatty acid constituents to give the results shown in Table 4 below, in which, and hereinafter, the symbols Ln, L, O, S, P and Po denote γ-linolenic, linoleic, oleic, stearic, palmitic and palmitooleic acids, respectively. For example, PSO in the table means that the triglyceride is a mixed glycerin triester of palmitic, stearic and oleic acids and OL in the table means that the diglyceride is a mixed glycerin diester of oleic and linoleic acids. Although other tri- and diglycerides including PLnLn, OLLn, LLL, SOO, PSS and PL could be detected by the chromatographic analysis, they are omitted in Table 4 since the amount of each of them was only 0.6% or smaller.

TABLE 4

| Triglycerides, % | | | | | | | | | | | | | | Diglycerides, % | | | |
|---|---|---|---|---|---|---|---|---|---|---|---|---|---|---|---|---|---|
| OLnLn | PLLn | OOLn | OLL | PLL | OOL | SOln | SLL | POL | SSLn | SOL | OOO | POO | PPO | PPoO | PPS | SSS | OLn | OL | OO | PO |
| 0.7 | 1.7 | 2.5 | 1.5 | 4.3 | 5.6 | 1.0 | 2.7 | 10.4 | 3.8 | 2.0 | 5.8 | 24.4 | 22.9 | 2.6 | 5.5 | 1.2 | 6.3 | 12.5 | 27.1 | 54.1 |

The above described fungus body lipid mixture was dissolved in hexane, acetone, petroleum ether or ethyl alcohol in a concentration of 5 to 40% and the solution was chilled and kept at a temperature of +4° or −20° C. for 16 to 24 hours so that the lipids were partially crystallized and precipitated in the solution. The precipitates were freed from the mother liquor by centrifugal separation followed by drying of the precipitates and evaporation of the solvent from the mother liquor to determine the weights of the crystallized and uncrystallized fractions. The results are shown in Table 5 below, in which, and also hereinafter, the symbols C and L indicate the crystallized and uncrystallized fractions, respectively.

Each of the crystallized and uncrystallized fractions was further analyzed by the gas chromatography for the % composition of the fatty acids to give the results shown in Table 5, by the thin layer chromatography for the lipid type composition and by the high-performance liquid chromatography for the % composition of the glycerides relative to the combination of the fatty acids in the respective glycerides to give the results shown in Table 6. The symbols TG, 1,3-DG and 1,2-DG in Table 6 denote a triglyceride, 1,3-diglyceride and 1,2-diglyceride, respectively.

TABLE 5

| Solvent | Temperature, °C. | Concentration, % | Fraction | % of overall lipids | Fatty acid, % | | | | | |
|---|---|---|---|---|---|---|---|---|---|---|
| | | | | | P | Po | S | O | L | Ln |
| — | — | — | (Starting lipids) | — | 30.5 | 1.9 | 4.6 | 45.7 | 9.7 | 6.0 |
| Hexane | −20 | 5 | C | 24.8 | 48.4 | — | 8.0 | 37.5 | 2.6 | 1.7 |
| | | | L | 75.2 | 24.7 | 2.2 | 3.5 | 49.1 | 11.7 | 7.1 |
| | | 10 | C | 31.9 | 49.3 | — | 7.8 | 37.0 | 2.6 | 1.8 |
| | | | L | 68.1 | 23.0 | 2.2 | 3.0 | 49.9 | 12.5 | 7.5 |
| | | 20 | C | 36.0 | 48.4 | 0.1 | 6.6 | 38.3 | 3.3 | 2.0 |
| | | | L | 64.0 | 22.4 | 2.3 | 3.1 | 50.6 | 12.4 | 7.6 |
| | | 40 | C | 41.6 | 45.3 | — | 5.8 | 39.2 | 5.0 | 3.0 |
| | | | L | 58.4 | 22.8 | 2.3 | 3.1 | 50.5 | 12.2 | 7.5 |
| | 4 | 40 | C | 27.5 | 42.5 | 0.3 | 5.9 | 41.4 | 5.3 | 3.5 |
| | | | L | 72.5 | 27.1 | 2.1 | 4.1 | 47.9 | 10.7 | 7.0 |
| Acetone | −20 | 5 | C | 42.8 | 44.9 | 0.2 | 5.7 | 40.2 | 5.0 | 2.7 |
| | | | L | 57.2 | 22.0 | 2.3 | 2.9 | 50.4 | 12.5 | 8.1 |
| | | 10 | C | 49.7 | 42.5 | 0.3 | 6.3 | 41.1 | 5.5 | 2.7 |
| | | | L | 50.3 | 21.1 | 2.5 | 2.9 | 50.8 | 12.7 | 8.3 |
| | | 20 | C | 63.8 | 38.5 | 0.5 | 5.6 | 43.6 | 6.7 | 3.6 |
| | | | L | 36.2 | 19.7 | 2.3 | 2.7 | 50.4 | 13.7 | 9.7 |
| | | 40 | C | 81.7 | 34.6 | 0.6 | 5.0 | 45.4 | 8.2 | 4.7 |
| | | | L | 18.3 | 19.8 | 2.4 | 2.7 | 48.9 | 14.2 | 10.1 |
| Acetone | 4 | 5 | C | 46.4 | 42.0 | 0.3 | 5.5 | 41.2 | 5.8 | 3.7 |
| | | | L | 53.6 | 23.3 | 2.3 | 3.0 | 50.0 | 12.2 | 7.5 |
| | | 10 | C | 46.8 | 42.7 | 0.3 | 5.5 | 40.9 | 5.8 | 3.5 |
| | | | L | 53.2 | 22.4 | 2.4 | 3.1 | 50.5 | 12.4 | 7.5 |
| | | 20 | C | 56.8 | 39.4 | 0.4 | 5.1 | 42.5 | 6.9 | 4.2 |
| | | | L | 43.2 | 22.5 | 2.3 | 3.0 | 50.0 | 12.5 | 8.0 |
| | | 40 | C | 67.3 | 36.7 | 0.5 | 4.7 | 44.1 | 7.7 | 4.8 |
| | | | L | 32.7 | 22.6 | 2.4 | 3.0 | 50.0 | 12.4 | 7.9 |
| Petroleum ether | −20 | 5 | C | 19.9 | 50.7 | — | 8.8 | 36.5 | 1.5 | 1.4 |
| | | | L | 80.1 | 26.0 | 2.2 | 3.7 | 48.6 | 11.3 | 6.9 |
| | | 10 | C | 21.4 | 48.7 | — | 8.6 | 37.4 | 2.9 | 2.0 |
| | | | L | 78.6 | 26.3 | 2.2 | 3.8 | 48.5 | 11.0 | 7.0 |
| | | 20 | C | 20.8 | 45.8 | — | 7.9 | 39.2 | 3.5 | 2.4 |
| | | | L | 79.2 | 26.9 | 2.2 | 3.9 | 48.1 | 10.8 | 6.8 |
| | | 40 | C | 27.0 | 43.9 | — | 6.9 | 40.1 | 4.6 | 3.0 |
| | | | L | 73.0 | 26.6 | 2.1 | 3.8 | 48.4 | 10.9 | 6.9 |
| | 4 | 40 | C | 34.4 | 42.9 | 0.2 | 6.5 | 40.9 | 5.0 | 3.2 |
| | | | L | 65.6 | 24.1 | 2.3 | 3.6 | 48.8 | 11.5 | 6.9 |
| Ethyl alcohol | −20 | 5 | C | 83.8 | 37.0 | 0.6 | 4.3 | 44.3 | 7.5 | 3.9 |
| | | | L | 16.2 | 16.0 | 2.4 | 2.3 | 51.8 | 14.5 | 10.8 |
| | 4 | 5 | C | 73.7 | 37.2 | 0.5 | 5.2 | 44.3 | 7.3 | 3.9 |
| | | | L | 26.3 | 16.6 | 2.6 | 2.6 | 51.1 | 14.5 | 10.5 |

TABLE 6

| Solvent | Temperature, °C. | Concentration, % | Fraction | % of overall lipids | % of lipid type | | | Triglycerides, % | | | | | | |
|---|---|---|---|---|---|---|---|---|---|---|---|---|---|---|
| | | | | | TG | 1,3-DG | 1,2-DG | OLnLn | PLLn | OOLn | OLL | PLL | OOL | SOLn |
| Hexane | −20 | 10 | C | 31.9 | 88.4 | 2.8 | 8.6 | — | — | — | — | — | 0.6 | — |
| | | | L | 68.1 | 75.3 | 4.2 | 19.0 | 0.4 | 2.1 | 3.0 | 1.6 | 5.2 | 7.0 | 1.2 |
| | | 40 | C | 41.6 | 84.9 | 4.0 | 10.1 | — | 0.9 | — | — | 2.3 | 3.1 | — |
| | | | L | 58.4 | 73.7 | 6.5 | 18.3 | 0.5 | 2.5 | 3.6 | 1.7 | 6.8 | 8.0 | 1.6 |
| | 4 | 40 | C | 27.5 | 86.9 | 4.4 | 8.3 | — | 0.7 | 1.1 | 0.5 | 2.5 | 3.1 | — |
| | | | L | 72.5 | 79.5 | 5.4 | 14.7 | 0.4 | 1.9 | 2.9 | 1.4 | 5.1 | 7.1 | 1.4 |
| Acetone | −20 | 10 | C | 49.7 | 89.1 | 2.0 | 8.4 | — | 0.4 | 0.7 | — | 1.3 | 2.0 | 0.9 |
| | | | L | 50.3 | 73.3 | 5.2 | 19.6 | 1.1 | 2.9 | 3.8 | 1.5 | 7.3 | 9.4 | 0.8 |
| | 4 | 10 | C | 46.8 | 90.5 | 2.3 | 6.9 | — | 0.8 | 1.2 | 0.8 | 2.4 | 2.9 | 1.0 |
| | | | L | 53.2 | 76.9 | 4.2 | 17.4 | 0.5 | 2.5 | 3.6 | 1.4 | 6.1 | 8.2 | 1.5 |
| Petroleum ether | −20 | 10 | C | 21.4 | 87.9 | 2.9 | 9.2 | 0.6 | 0.4 | 0.7 | — | 0.2 | 1.3 | 1.7 |
| | | | L | 78.6 | 78.3 | 4.0 | 16.7 | 0.8 | 2.1 | 2.6 | 1.1 | 5.1 | 6.4 | 0.9 |
| | | 40 | C | 27.0 | 86.4 | 2.6 | 11.0 | — | 0.4 | 0.7 | 0.7 | 1.6 | 2.5 | 0.8 |

TABLE 6-continued

| | | | | | | | | | | | | | |
|---|---|---|---|---|---|---|---|---|---|---|---|---|---|
| | | | L | 73.0 | 79.1 | 3.9 | 15.7 | 0.6 | 1.5 | 2.7 | 1.1 | 4.8 | 6.8 | 1.0 |
| | 4 | 40 | C | 34.4 | 86.4 | 2.9 | 10.3 | — | 0.6 | 0.9 | 0.5 | 2.1 | 2.7 | 0.6 |
| | | | L | 65.6 | 76.6 | 4.2 | 16.0 | 0.9 | 1.8 | 3.1 | 1.2 | 5.3 | 7.4 | 1.3 |
| Ethyl | 4 | 5 | C | 73.7 | 92.3 | 2.0 | 4.9 | — | 0.6 | 1.5 | 0.7 | 2.7 | 3.9 | 1.1 |
| alcohol | | | L | 26.3 | 53.5 | 7.8 | 30.5 | 2.0 | 5.6 | 5.5 | 3.1 | 10.3 | 10.6 | — |

| Triglycerides, % | | | | | | | | | | Diglycerides, % | | | |
|---|---|---|---|---|---|---|---|---|---|---|---|---|---|
| SLL | POL | SSLn | SOL | OOO | POO | PPO | PPoO | PPS | SSS | OLn | OL | OO | PO |
| — | 0.9 | 1.9 | 3.7 | 0.9 | 5.5 | 63.1 | — | 18.8 | 4.2 | — | — | 18.2 | 81.8 |
| 4.1 | 15.0 | 3.5 | 1.3 | 8.6 | 33.3 | 4.8 | 4.4 | 0.7 | — | 8.8 | 14.0 | 31.6 | 45.6 |
| 1.0 | 3.7 | 7.5 | — | 2.6 | 10.7 | 47.2 | 2.9 | 13.5 | 2.6 | — | — | — | 98.0 |
| 4.3 | 20.7 | — | 1.2 | 8.9 | 31.2 | 3.7 | 4.7 | 1.2 | — | 7.4 | 14.8 | 27.8 | 50.0 |
| 0.3 | 0.8 | 2.0 | 0.6 | 4.5 | 16.8 | 64.3 | 1.9 | 16.8 | 1.0 | — | — | 32.0 | 68.0 |
| 3.8 | 13.5 | 3.8 | 2.2 | 8.0 | 30.0 | 13.5 | 3.4 | 3.4 | — | 8.6 | 13.8 | 29.3 | 48.3 |
| 1.0 | 6.6 | 4.6 | 3.5 | 2.1 | 18.7 | 43.0 | 1.9 | 11.3 | 0.3 | — | — | 38.5 | 61.5 |
| 5.0 | 18.9 | — | 0.8 | 10.2 | 30.6 | — | 4.9 | — | — | 5.9 | 12.9 | 30.6 | 50.6 |
| 1.4 | 4.3 | 4.3 | 3.0 | 3.0 | 13.9 | 44.8 | 1.7 | 12.7 | 2.0 | — | 17.4 | 30.4 | 52.2 |
| 4.2 | 18.7 | — | 1.6 | 9.3 | 33.7 | 2.5 | 4.3 | — | — | 8.5 | 14.1 | 29.6 | 47.9 |
| 2.9 | 0.2 | — | — | 1.1 | 5.0 | 61.3 | 0.6 | 20.2 | 3.5 | — | — | — | 98.0 |
| 3.2 | 13.2 | 4.6 | 1.9 | 7.6 | 31.4 | 12.8 | 4.4 | 2.9 | — | 5.3 | 14.0 | 33.3 | 47.4 |
| 1.3 | 4.1 | 2.7 | 3.4 | 2.3 | 11.5 | 48.7 | 1.3 | 13.8 | 3.4 | — | — | 39.0 | 60.9 |
| 3.2 | 18.3 | — | — | 7.9 | 30.9 | 13.9 | 3.8 | 3.0 | — | 6.7 | 13.3 | 26.7 | 53.3 |
| 1.4 | 5.1 | 2.3 | 2.8 | 3.0 | 12.3 | 50.7 | 1.3 | 13.5 | — | — | 12.0 | 28.0 | 60.0 |
| 3.7 | 14.0 | 3.8 | 2.2 | 8.4 | 32.4 | 8.1 | 3.3 | 1.7 | — | 7.5 | 16.4 | 29.9 | 44.8 |
| 1.4 | 9.5 | 4.2 | 2.5 | 3.5 | 26.7 | 29.4 | 2.7 | 7.4 | 1.0 | — | 27.2 | 36.4 | 45.5 |
| 9.6 | 14.5 | — | — | 16.4 | 15.2 | 0.6 | — | 3.3 | — | 3.0 | 10.5 | 20.3 | 66.1 |

As is clear from Table 5 showing the results of the experiments of fractional crystallization using hexane, acetone, petroleum ether and ethyl alcohol as the solvent, good enrichment of γ-linolenic acid in the low-temperature fractional crystallization could be obtained in the uncrystallized fraction irrespective of the kind of the solvent by chilling the solution at +4° C. or −20° C. Namely, the content of γ-linolenic acid, denoted by Ln, in the uncrystallized fraction was at least 6.8% with the highest value of 10.8% in an experiment. It is noteworthy that the concentration of the lipid mixture in the solution had some influences on the fatty acid composition in the crystallized fraction consequently influencing the content of γ-linolenic acid in the uncrystallized fraction. This fact is suggestive of the possibility of a further increased efficiency of enriching or controlling the uncrystallized fraction in respect of the content of γ-linolenic acid by suitably selecting the solvent, concentration, chilling temperature and other parameters. It is also noted that the lipid mixture obtained as the uncrystallized fraction was depleted of the content of palmitic acid by almost 10% and somewhat enriched in the contents of oleic and linoleic acids in comparison with the lipid mixture before the fractional crystallization.

The results shown in Table 6 indicate that the content of triglycerides was higher in the crystallized fraction than in the uncrystallized fraction while the content of diglycerides was higher in the latter fraction than in the former. Namely, the glycerides containing γ-linolenic acid as the fatty acid constituent are composed of a somewhat increased amount of the diglycerides relative to the triglycerides. Further, fractionation took place of PPO, POO and PPS as the major triglycerides and PO and OO as the major diglycerides consequently leading to the enrichment of the glycerides containing γ-linolenic acid in the uncrystallized fraction.

In parallel with the above described fractional crystallization experiments, some more experiments were undertaken in the same manner as above excepting the replacement of the solvent with benzene, toluene, xylene or methyl alcohol without success in respect of the object of enrichment of γ-linolenic acid in the uncrystallized fraction.

I claim:

1. A method for fractionally extracting lipids from cultured fungus bodies of a filamentous fungus belonging to the genus of *Mortierella* containing lipids with solvents into fractions rich and lean in the content of the polar lipids or the neutral lipids which comprises the steps of:
    (a) disintegrating the fungus bodies by a mechanical action in a liquid medium of an alcohol containing water to cause extraction of a part of the lipids contained in the fungus bodies into the liquid medium;
    (b) separating the liquid medium containing the extracted lipids from the disintegrated fungus bodies to give a first fractional extract which is rich in the content of the polar lipids;
    (c) mixing the disintegrated fungus bodies separated from the first fractional extract with a hydrocarbon solvent in substantial absence of water to cause extraction of the residual fraction of the lipids contained in the fungus bodies; and
    (d) separating the hydrocarbon solvent containing the extracted lipids from the fungus bodies depleted of the lipids to give a second fractional extract which is lean in the content of the polar lipids.

2. The method of claim 1 wherein the alcohol is ethyl alcohol.

3. The method of claim 1 wherein the amount of the alcohol is in the range from 2 to 7 parts by weight per part by weight of the fungus bodies as dry.

4. The method of claim 1 wherein the amount of water in the liquid medium is in the range from 0.2 to 0.7 part by weight per part by weight of the alcohol.

5. The method of claim 1 wherein the hydrocarbon solvent is n-hexane or cyclohexane.

6. The method of claim 1 wherein the amount of the hydrocarbon solvent is in the range from 2 to 8 parts by weight per part by weight of the fungus bodies as dry.

7. The method of claim 1 wherein the amount of water in the mixture of the hydrocarbon solvent and the fungus bodies is 0.05 part by weight or smaller per part by weight of the hydrocarbon solvent.

* * * * *